(12) United States Patent
Yoshinaga et al.

(10) Patent No.: US 7,153,523 B2
(45) Date of Patent: Dec. 26, 2006

(54) BIOLOGICALLY ABSORBABLE POLYHYDROXYCARBOXYLIC ACID AND PRODUCTION METHOD THEREOF

(75) Inventors: Kazuhiko Yoshinaga, Sodegaura (JP); Hideyuki Akieda, Sodegaura (JP)

(73) Assignee: Mitsui Chemicals, Inc., Tokyo (JP)

(*) Notice: Subject to any disclaimer, the term of this patent is extended or adjusted under 35 U.S.C. 154(b) by 483 days.

(21) Appl. No.: 10/322,458

(22) Filed: Dec. 19, 2002

(65) Prior Publication Data
US 2003/0129232 A1    Jul. 10, 2003

(30) Foreign Application Priority Data
Dec. 26, 2001   (JP) ............................. 2001-394565

(51) Int. Cl.
*A61K 9/16*    (2006.01)
*C08G 63/00*   (2006.01)

(52) U.S. Cl. ................... 424/468; 528/355; 528/354

(58) Field of Classification Search ............... 424/426, 424/78.08, 457
See application file for complete search history.

(56) References Cited

U.S. PATENT DOCUMENTS

| 4,677,191 A | 6/1987 | Tanaka et al. |
| 4,728,721 A | 3/1988 | Yamamoto et al. |
| 5,304,377 A * | 4/1994 | Yamada et al. ............. 424/426 |
| 6,113,943 A * | 9/2000 | Okada et al. ............... 424/457 |

FOREIGN PATENT DOCUMENTS

| EP | 0 500 098 A2 | 8/1992 |
| EP | 0 664 309 A2 | 7/1995 |
| EP | 0 755 956 A2 | 1/1997 |
| JP | 61-28521 A | 2/1986 |
| JP | 61-236820 A | 10/1986 |
| JP | 62-54760 A | 3/1987 |
| JP | 6-49185 A | 2/1994 |
| JP | 11-1443 A | 1/1999 |
| JP | 11-106499 A | 4/1999 |

* cited by examiner

*Primary Examiner*—MP Woodward
(74) *Attorney, Agent, or Firm*—Buchanan Ingersoll & Rooney PC

(57) ABSTRACT

A biologically absorbable polyhydroxycarboxylic acid in which a content of water-soluble acid components is not more than 0.07 mol/kg in terms of monobasic acids, and which has a weight average molecular weight of 4,000 to 100,000 and contains neither a catalyst nor an organic solvent, and a production method thereof.

4 Claims, No Drawings

BIOLOGICALLY ABSORBABLE POLYHYDROXYCARBOXYLIC ACID AND PRODUCTION METHOD THEREOF

BACKGROUND OF THE INVENTION

1. Field of the Invention

The present invention relates to a polyhydroxycarboxylic acid which is useful as a biologically absorbable material, particularly as a sustained-releasable material, and a production method thereof.

2. Description of the Related Art

Some examples of methods for producing a polyhydroxycarboxylic acid which is usable as a biologically absorbable material, particularly as a sustained-releasable material, are known.

For example, there are a method in which lactic acid and glycolic acid are polycondensed in the presence of a strongly acidic ion exchange resin as a catalyst (Japanese Patent Publication No. 21166/1989), and a method in which lactic acid and glycolic acid are polycondensed in the presence of an inorganic solid acid (Japanese Patent Publication No. 78425/1994). Polyhydroxycarboxylic acids obtained by these polycondensation methods have a fault that they contain low molecular-weight oligomers and monomers in a large amount. The oligomers and monomers cause unusual initial release (initial burst) of a drug when such polyhydroxycarboxylic acids are used as a base material of microcapsule.

On the other hand, as a method for decreasing the amount of low molecular-weight oligomers and monomers contained in the polyhydroxycarboxylic acid, for example, Japanese Patent Nos. 2551756 and 3200706 disclose a method of washing the polymer with water or a mixed solution of water and a water-soluble organic solvent.

However, the method of washing the polymer with water has a problem that water must be removed from the washed polymer as much as possible so as to prevent occurrence of hydrolysis of the polyhydroxycarboxylic acid during long-time storage. Such drying step for removing water from the polymer takes long time. Furthermore, if the organic solvent is used, it is difficult to handle the polymer and to remove the residual organic solvent therefrom because the deposited polymer contains the organic solvent and thereby becomes a viscous rice-cake-like mass.

As described above, with the conventional polymerization methods, it is difficult to obtain a polyhydroxycarboxylic acid which has low contents of low molecular-weight oligomers and monomers and has good releasability of a drug. Furthermore, a method of purifying the polyhydroxycarboxylic acid also has various problems. Accordingly, it is desired to develop a polyhydroxycarboxylic acid which has low contents of low molecular-weight oligomers and monomers, contains no organic solvent and is useful as a biologically absorbable material. Furthermore, it is desired to develop a method which is industrially advantageous for producing the polyhydroxycarboxylic acid.

SUMMARY OF THE INVENTION

An object of the present invention is to provide a polyhydroxycarboxylic acid which is useful as a biologically absorbable material, contains neither a catalyst nor an organic solvent and has low contents of low molecular-weight oligomers and monomers, and an efficient production method of the polyhydroxycarboxylic acid.

The present inventors have made intensive studies to achieve the object. As the result, they found that it is possible to obtain a polyhydroxycarboxylic acid having low contents of low molecular-weight oligomers and monomers, when a hydroxycarboxylic acid as a raw material is heated while an inert gas is allowed to flow through the reactor. This reaction is conducted with no catalyst. The present invention has been completed by these investigations.

The low molecular-weight oligomers and monomers contained in the polyhydroxycarboxylic acid can be quantified as water-soluble acid components. In other words, the low molecular-weight oligomers can be distinguished, as water-soluble components, from the polyhydroxycarboxylic acid of the present invention.

Hereinafter, in the present specification, the phrase "content of water-soluble acid components" is defined as a total of the content of hydroxycarboxylic acid as a raw material contained in the polymer and the content of a low molecular-weight oligomer derived from the raw material wherein they are water-soluble acid components.

The present invention is a biologically absorbable polyhydroxycarboxylic acid in which a content of water-soluble acid components is not more than 0.07 mol/kg in terms of monobasic acids, and which has a weight average molecular weight of 4,000 to 100,000 and contains neither a catalyst nor an organic solvent.

Further, the present invention is a production method of the biologically absorbable polyhydroxycarboxylic acid of claim 1, which includes a step of heating a hydroxycarboxylic acid or its oligomer while at least 1 dm$^3$ of an inert gas in cumulative total based on 1 kg of the polyhydroxycarboxylic acid to be produced is allowed to flow through a reactor.

DETAILED DESCRIPTION OF THE PREFERRED EMBODIMENTS

In the present invention, the polyhydroxycarboxylic acid is a polymer of a hydroxycarboxylic acid. The hydroxycarboxylic acid is, for example, lactic acid, glycolic acid, hydroxypropionic acid, or hydroxycaproic acid.

As the polyhydroxycarboxylic acid, one which decomposes in a living body at a proper speed is preferred. Preferred examples thereof include a homopolymer of lactic acid or glycolic acid and a copolymer of lactic acid and glycolic acid. A particularly preferred example thereof is a copolymer wherein the molar ratio of lactic acid/glycolic acid is from 95/5 to 40/60.

The weight average molecular weight of the polyhydroxycarboxylic acid is 4,000 to 100,000, preferably 7,000 to 100,000. When the weight average molecular weight is 4,000 or higher, excessively fast decomposition of the polyhydroxycarboxylic acid in a living body does not occur easily, and the content of water-soluble acid components contained in the polymer becomes low. Meanwhile, when the weight average molecular weight is 100,000 or lower, excessively slow decomposition of the polyhydroxycarboxylic acid in a living body does not occur easily. The method of measuring the molecular weight is, for example, a gel permeation chromatography method using a polystyrene as a standard material.

The content of the water-soluble acid components in the polyhydroxycarboxylic acid is not more than 0.07 mol/kg, preferably not more than 0.03 mol/kg, in terms of monobasic acids, because the polymer can show a stable sustained releasability of drug when it is used as a sustained-releasable material. As a method of measuring the content of the water-soluble acid components, for example, there is a method comprising the steps of dissolving 0.5 g of the polyhydroxycarboxylic acid into 50 cm$^3$ of dichloromethane completely, adding 40 cm$^3$ of distilled water thereto, shaking the mixture for 10 minutes, separating the mixture into an organic layer and a water layer, adding 30 cm$^3$ of distilled water into the organic layer, shaking the mixture for 10 minutes, separating the mixture into an organic layer and a water layer, mixing the water layer with the previously obtained water layer, and subjecting the resulting water layer to neutralization-titration using a 0.01N sodium hydroxide solution.

As described above, the hydroxycarboxylic acid used as a raw material in producing the polyhydroxycarboxylic acid is, for example, lactic acid, glycolic acid, hydroxypropionic acid, and hydroxycaproic acid.

As the hydroxycarboxylic acid, there are D isomer, L isomer and a mixture thereof. All of them can be used. Furthermore, it is possible to solely use one of these hydroxycarboxylic acids, and to use them in combination of two or more.

Furthermore, an oligomer of a hydroxycarboxylic acid can also be used as a raw material in producing the polyhydroxycarboxylic acid. The oligomer usually has one or more carboxylic terminals and hydroxyl groups in the molecule. The oligomer is, for example, a dimer, trimer or tetramer of the hydroxycarboxylic acid. In addition, it is possible to use one having a weight average molecular weight of lower than 4,000 obtained by subjecting a polycondensation of hydroxycarboxylic acid in accordance with a known method.

Some of these hydroxycarboxylic acids are provided generally in the form of an aqueous solution. They can also be used as the raw material.

In the present invention, an inert gas is preferably allowed to flow through a reactor upon polymerization of the hydroxycarboxylic acid.

The inert gas is not particularly limited as long as it does not affect the polymerization reaction. From an economical standpoint, for example, argon, nitrogen, carbon dioxide are preferred, and nitrogen is particularly preferred among them.

The amount of water contained in the inert gas is not particularly a concern as long as it is a general amount of water contained in an inert gas which is used in industrial applications. However, it is preferable to use an inert gas wherein the amount of water is reduced in accordance with a known method. The smaller the amount of the water contained in the inert gas, the more advantageous it is. For example, it is possible to use a nitrogen gas having a dew point controlled into from −65 to −70° C. by use of a cooling trap.

As for the amount of flow of the inert gas, the inert gas is preferably allowed to flow in a volume of at least 1 dm$^3$, more preferably at least 10 dm$^3$, particularly preferably at least 100 dm$^3$, most preferably at least 1,000 dm$^3$ in cumulative total, based on 1 kg of the polymer to be produced, since the content of the water-soluble acid components becomes low and a significant decrease in polymerization speed does not occur. The wording "cumulative total" refers to a cumulative total of a volume of the inert gas allowed to flow.

An amount of flow per unit of time (hereinafter referred to as "flow rate") of the inert gas is not particularly limited. The inert gas may be allowed to flow at a fixed flow rate, or the flow rate may be changed as required.

The inert gas may be allowed to flow continuously or intermittently. When the inert gas to flow intermittently, the above flow rate indicates a rate in a period during which the inert gas is actually flowing, and the above flow time indicates a total time during which the inert gas has actually been allowed to flow.

The inert gas may be allowed to flow only during a certain period in the polymerization or through the whole polymerization period continuously or intermittently.

The wording "polymerization period" indicates a period during which an operation for increasing the molecular weight by the polycondensation reaction is carried out. More specifically, it indicates a period of from the time that the polycondensation reaction is initiated by heating after the hydroxycarboxylic acid or its oligomer as a raw material is charged into a reactor, to the time that the polycondensation reaction is terminated by cooling after a predetermined molecular weight is attained.

Furthermore, it is also acceptable that a once-isolated polyhydroxycarboxylic acid is heated again to be molten and the inert gas is allowed to flow until the polyhydroxycarboxylic acid reaches a predetermined weight average molecular weight and a predetermined content of water-soluble acid components. This operation can be performed, for example, in a case where the content of the water-soluble acid components is reduced when the polyhydroxycarboxylic acid already has the predetermined weight average molecular weight.

An internal pressure in the reactor is not particularly limited but is preferably an atmospheric pressure since the reactor can be simplified.

How the inert gas is allowed to flow is not particularly limited. However, it is preferable to cause the inert gas to flow on an interface between the molten polymer and a gas phase or blow the inert gas into the molten polymer. It is particularly preferable to blow the inert gas into the molten polymer.

After passing though the reactor, the inert gas may be released in air. Alternatively, the inert gas may be allowed to flow through the reactor again after water and the like contained in the inert gas are reduced by a known device such as a low-temperature trap.

In the present invention, the reaction temperature must be set at within temperatures ranging from a temperature at which the polymer in the reaction is in a molten state to the decomposition point of the polyhydroxycarboxylic acid to be produced. When the reaction temperature is lower than the foregoing temperature range, efficiency of removal of water produced by the polycondensation lowers, so that the reaction speed lowers, which is inefficient, and efficiency of removal of the water-soluble acid components lowers. Meanwhile, when the reaction temperature is higher than the foregoing temperature range, the polymer is liable to be decomposed. For example, in the case of a copolymer with a molar ratio of lactic acid/glycolic acid of 95/5 to 40/60, the reaction temperature is preferably within a range from 120° C. to the decomposition temperature of the copolymer, more preferably 150 to 240° C., particularly preferably 170 to 230° C.

Furthermore, to prevent the hydroxycarboxylic acid as a raw material and water from distilling out simultaneously upon elevation of the reaction temperature, the reaction temperature may be elevated gradually from low temperatures and eventually elevated to the aforementioned temperature range after the hydroxycarboxylic acid as a raw material is formed into an oligomer.

In the present invention, the polymerization can be carried out in the absence of a catalyst or in the presence of a catalyst insoluble in the polyhydroxycarboxylic acid. The polymerization is preferably carried out in the absence of a catalyst because no catalyst remains in the polyhydroxycarboxylic acid to be obtained.

Specific examples of the catalyst insoluble in the polyhydroxycarboxylic acid include inorganic solid acids such as an activated clay, acid clay, aluminum silicate, and magnesium silicate.

In the present invention, a polymerizer is not particularly limited, but it is preferable that an apparatus capable of performing high speed agitation so as to widen a contact area between the molten polyhydroxycarboxylic acid and the inert gas be provided.

Generally, the polyhydroxycarboxylic acid obtained by the production method of the present invention does not require a purifying operation in particular. However, an operation of removing solid impurities by means of filtration or the like may be performed.

The biologically absorbable polyhydroxycarboxylic acid of the present invention contains no catalyst and organic solvent which may adversely affect a living body. Thus, it can be preferably used as a biologically absorbable material. Furthermore, since the biologically absorbable polyhydroxycarboxylic acid of the present invention has only a small content of water-soluble acid components which cause abnormal initial release of a drug when used as a base material of sustained-releasable drug, it can be particularly preferably used as the base material of the sustained-releasable drug.

The form of the sustained-releasable drug is not particularly limited and may be a microcapsule, a pellet, a stick, a needle, a film, a granule or the like. Drugs which may be contained in these forms are not particularly limited. Illustrative examples of such drugs include an antineoplastic drug, biologically active peptide, hormone drug, antibiotic, antipyretic, analgesic, antiphlogistic, antitussive, sedative, muscle relaxant, antiepileptic, antiulcer drug, antidepressant, antiallergic drug, cardiac stimulant, antiarrhythmic drug, vasodilator drug, hypotensive diuretic, antidiabetic drug, anticoagulant drug, hemostatic drug, antituberculosis agent, narcotic antagonist, bone resorption restrainer, bone formation accelerator, and vascularization restrainer.

The biologically absorbable polyhydroxycarboxylic acid of the present invention can be processed into an appropriate form such as a mesh, a film, a needle, a thread, a fiber or a stick so as to be used as a raw material of a biodegradable medical product. Illustrative examples of the implantable medical product include an implant for curing a periodontal disease, a pin for orthopedics, a clamp, a screw, a plate, a clip, a substitute bone, a non-permanent intrauterine device, a tube, a capillary, a reinforcing bone pin, a bandage, a fracture pad, absorption paper, an expulsion bandage, a cloth, a sponge, a dental filling material, a suture, and a film for treating a wound.

The biologically absorbable polyhydroxycarboxylic acid of the present invention can be used as a base material of sustained-releasable agricultural chemicals. Agricultural chemical active ingredients to be contained are not particularly limited and are exemplified by ingredients having effects of a pesticide, bactericide and herbicide.

The biologically absorbable polyhydroxycarboxylic acid of the present invention can be used as a base material to be sustained-releasable fertilizers. Fertilizer ingredients to be contained are not particularly limited, and any fertilizer ingredients which are used in growth periods of various crops may be used. Illustrative examples of the fertilizer ingredients include potassium sulfate, potassium phosphate, potassium chloride, ammonium sulfate, ammonium phosphate, ammonium nitrate, and ammonium chloride.

Hereinafter, the present invention will be further described with reference to Examples. However, the present invention shall not be limited by these Examples in any way.

Molecular weights in the following Examples were measured by gel permeation chromatography using a polystyrene as a standard.

Conditions for Measuring Molecular Weight: A molecular weight was measured by use of shodex GPC system-11 (manufactured by Showa Denko Co., Ltd.), PLgel 5-μm MIXED-C (manufactured by Polymer Laboratory Co., Ltd.) as a column, and chloroform as a solvent, at a flow rate of 1.0 cm$^3$/min and a column temperature of 40° C.

EXAMPLE 1

Into a 200-ml four-neck round-bottom flask, 100 g of 90% DL-lactic acid solution (manufactured by Musashino Nusan Co., Ltd.) and 36 g of 70% glycolic acid solution (manufactured by Otsuka Kagaku Co., Ltd.) were charged, and then stirred to prepare a homogeneous solution. The reactor was immersed in an oil bath at 165 to 170° C., and then the temperature was maintained for 2 hours while water was distilled out and removed. At the moment, the weight average molecular weight thereof was not more than 1,000. Then, nitrogen gas with a dew point of −65 to −70° C. was allowed to flow through the reactor continuously at a flow rate of 3.6 dm$^3$/min and at a temperature of the oil bath of 185 to 190° C. so as to cause polymerization to take place. After the temperature and the nitrogen flow rate were maintained for 45 hours, an opalescent polymer was obtained.

The weight average molecular weight and dispersity of the obtained polymer were 18,500 and 2.90 respectively. The content of water-soluble acid components in the polymer was 0.007 mol/kg. A total of the nitrogen which flowed through the reactor during the polymerization was 106,000 dm$^3$ per 1 kg of the obtained polymer.

EXAMPLE 2

Into a 200-ml four-neck round-bottom flask, 100 g of 90% DL-lactic acid solution and 19 g of 70% glycolic acid solution were charged, and then stirred to prepare a homogeneous solution. The reactor was immersed in an oil bath at 165 to 170° C., and then the temperature was maintained for 2 hours while water was distilled out and removed. Then, nitrogen gas with a dew point of −65 to −70° C. was allowed to flow through the reactor continuously at a flow rate of 5.0 dm$^3$/min and at a temperature of the oil bath of 225 to 230° C. so as to cause polymerization to take place. After the temperature and the nitrogen flow rate were maintained for 18.5 hours, an opalescent polymer was obtained.

The weight average molecular weight and dispersity of the obtained polymer were 36,000 and 3.50 respectively. The content of water-soluble acid components in the polymer was 0.001 mol/kg. A total of the nitrogen which flowed through the reactor during the polymerization was 68,000 dm$^3$ per 1 kg of the obtained polymer.

EXAMPLE 3

Into a 1,000-ml four-neck round-bottom flask, 500 g of 90% DL-lactic acid solution and 181 g of 70% glycolic acid solution were charged, and then stirred to prepare a homogeneous solution. The reactor was immersed in an oil bath at 165 to 170° C., and then the temperature was maintained for 3.5 hours while water was distilled out and removed. Then, nitrogen gas with a dew point of −65 to −70° C. was allowed to flow through the reactor continuously at a flow rate of 5.0 dm³/min and at a temperature of the oil bath of 205 to 210° C. so as to cause polymerization to take place. After the temperature and the nitrogen flow rate were maintained for 22.5 hours, an opalescent polymer was obtained.

The weight average molecular weight and dispersity of the obtained polymer were 17,100 and 3.06 respectively. The content of water-soluble acid components in the polymer was 0.010 mol/kg. A total of the nitrogen which flowed through the reactor during the polymerization was 14,800 dm³ per 1 kg of the obtained polymer.

EXAMPLE 4

Into a 200-ml four-neck round-bottom flask, 100 g of 90% DL-lactic acid solution and 36 g of 70% glycolic acid solution were charged, and then stirred to prepare a homogeneous solution. The reactor was immersed in an oil bath at 165 to 170° C., and then the temperature was maintained for 2 hours while water was distilled out and removed. Then, nitrogen with a dew point of −65 to −70° C. was allowed to flow through the reactor continuously at a flow rate of 1.0 dm³/min and at a temperature of the oil bath of 185 to 190° C. so as to cause polymerization to take place. After the temperature and the nitrogen flow rate were maintained for 20 hours, an opalescent polymer was obtained.

The weight average molecular weight and dispersity of the obtained polymer were 10,100 and 2.51 respectively. The content of water-soluble acid components in the polymer was 0.02 1 mol/kg. A total of the nitrogen which flowed through the reactor during the polymerization was 13,000 dm³ per 1 kg of the obtained polymer.

EXAMPLE 5

Into a 1,000-ml four-neck round-bottom flask, 500 g of 90% DL-lactic acid solution and 181 g of 70% glycolic acid solution were charged, and then stirred to prepare a homogeneous solution. The reactor was immersed in an oil bath at 165 to 170° C., and then the temperature was maintained or 3.5 hours while water was distilled out and removed. Then, nitrogen gas with a dew point of −65 to −70° C. was allowed to flow through the reactor continuously at a flow rate of 1.0 dm³/min and at a temperature of the oil bath of 205 to 210° C. so as to cause polymerization to take place. After the temperature and the nitrogen flow rate were maintained for 17 hours, an opalescent polymer was obtained.

The weight average molecular weight and dispersity of the obtained polymer were 10,700 and 2.53, respectively. The content of water-soluble acid components in the polymer was 0.027 mol/kg. A total of the nitrogen which flowed through the reactor during the polymerization was 2,200 dm³ per 1 kg of the obtained polymer.

These results are summarized in Table 1. The amounts of water-soluble free acids in Examples 1 to 5 are values measured immediately after the polymerizations without carrying out any purification operation which may reduce the amounts of the water-soluble free acids.

COMPARATIVE EXAMPLES 1 AND 2

The results of an unpurified polymer by a production method of a prior art (Japanese Patent No. 2551756) are also shown in Table 1 as Comparative Examples. These Comparative Examples 1 and 2 are corresponding with Referential Example 1 (Lot No. 3-1) and Referential Example 4 of the above patent respectively.

TABLE 1

| | Weight Average Molecular Weight | Amount of Water-Soluble Acid Components (mol/kg) |
|---|---|---|
| Example 1 | 18,500 | 0.007 |
| Example 2 | 36,000 | 0.001 |
| Example 3 | 17,100 | 0.010 |
| Example 4 | 10,100 | 0.021 |
| Example 5 | 10,700 | 0.027 |
| Comp. Ex. 1 | 12,500 | 0.165 |
| Comp. Ex. 2 | 13,000 | 0.210 |

According to the present invention described above, a high-quality polyhydroxycarboxylic acid can be provided which has low contents of low molecular-weight oligomers and monomers causing an initial burst in a living body, contains neither a catalyst nor an organic solvent, and is useful as a biologically absorbable material. Further, the polyhydroxycarboxylic acid can be produced with good productivity.

The invention claimed is:

1. A production method of a biologically absorbable polyhydroxycarboxylic acid in which a content of water-soluble acid components is not more than 0.03 mol/kg in terms of monobasic acids, and which has a weight average molecular weight of 4,000 to 100,000 and contains neither a catalyst nor an organic solvent, which includes a step of heating a hydroxycarboxylic acid or its oligomer at atmospheric pressure while at least 1 dm³ of an inert gas in cumulative total based on 1 kg of the polyhydroxycarboxylic acid to be produced is allowed to flow through a reactor, said method using neither a catalyst nor an organic solvent.

2. The production method of claim 1, which the inert gas is one or more gases selected from the group consisting of argon, nitrogen and carbon dioxide.

3. The production method of claim 1, in which the heating step is conducted so that the reaction temperature is within a range from 120° C. to the decomposition temperature of the polymer.

4. The production method of claim 1, in which the polyhydroxycarboxylic acid is a polymer of one or more hydroxycarboxylic acids selected from the group consisting of lactic acid, glycolic acid, hydroxypropionic acid and hydroxycaproic acid.

* * * * *